United States Patent [19]

Kirsch et al.

[11] Patent Number: 5,800,165
[45] Date of Patent: Sep. 1, 1998

[54] DENTAL INSTRUMENT AND METHOD OF BLEACHING TEETH USING A LASER

[75] Inventors: Wolff M. Kirsch, Redlands; Yong Hua Zhu; Mahmoud Torabinejad, both of Loma Linda, all of Calif.

[73] Assignee: Loma Linda University Medical Center, Loma Linda, Calif.

[21] Appl. No.: 411,906

[22] Filed: Mar. 28, 1995

[51] Int. Cl.$^6$ .................................................. A61C 1/00
[52] U.S. Cl. .............................. 433/29; 433/80; 433/89; 433/215; 433/216
[58] Field of Search .......................... 433/29, 32, 80, 433/84, 85, 88, 89, 215, 216, 217.1

[56] References Cited

U.S. PATENT DOCUMENTS

| | | |
|---|---|---|
| Re. 31,815 | 1/1985 | Alfano . |
| 3,821,510 | 6/1974 | Mucheryan . |
| 4,290,433 | 9/1981 | Alfano . |
| 4,515,476 | 5/1985 | Ingmar . |
| 4,521,194 | 6/1985 | Myers et al. . |
| 4,641,912 | 2/1987 | Godenberg . |
| 4,661,070 | 4/1987 | Friedman . |
| 4,784,135 | 11/1988 | Blum et al. . |
| 4,826,431 | 5/1989 | Fujimura et al. . |
| 4,940,411 | 7/1990 | Vassiliadis et al. . |
| 4,973,250 | 11/1990 | Milman . |
| 5,020,995 | 6/1991 | Levy . |
| 5,055,048 | 10/1991 | Vassiliadis et al. . |
| 5,090,908 | 2/1992 | Teumim-Stone . |
| 5,092,864 | 3/1992 | Hayes et al. . |
| 5,118,293 | 6/1992 | Levy . |
| 5,122,060 | 6/1992 | Vassiliadis et al. ............ 433/215 |
| 5,123,845 | 6/1992 | Vassiliadis et al. . |
| 5,192,279 | 3/1993 | Samuels et al. . |

(List continued on next page.)

OTHER PUBLICATIONS

"Generation of Superoxide Radicals in Aqueous and Ethanolic Solutions by Vacuum–UV Photolysis" Bielski, *methods in Enzymology*, 105:81–88, Copyright 1984.

"Selectivity, Efficiency, and Surface Characteristics of Hard Dental Tissues Ablated With ArF Pulsed Excimer Lasers" Neev, et al., *Lasers in Surgery and Medicine*, 11:499–510, 1991.

"Dye–Medicated Bactericidal Effect of He–Ne Laser Irradiation on Oral Microorganisms" Okamoto, et al., *Lasers in Surgery and Medicine*, 12:450–458, 1992.

"Excimer lasers in dentistry: future possibilities with advanced technology" Frentzen, et al., *Quintessence International*, 23:2, pp. 117–133, 1992.

"$CO_2$ laser and the diagnosis of occlusal caries: in vitro study" Longbottom, et al., *Jouranl of Dentistry*, 21:234–239, 1993.

"Effects of ArF: Excimer Laser Irradiation on Human Enamel and Dentin" Arima, et al., *Laser in Surgery and Medicine*, 13:97–105, 1993.

"Photolysis of oral bacteria and its potential use in the treatment of caries and periodontal disease" M. Wilson, *Jouranl of Applied Bacteriology*, 75:299–306, 1993.

"Bactericidal effect of laser light and its potential use in the treatment of plaque–related diseases" M. Wilson, *International Dental Journal*, 44:181–189, 1994.

*Primary Examiner*—John S. Hilten
*Attorney, Agent, or Firm*—Knobbe, Martens Olson & Bear, LLP

[57] ABSTRACT

A dental apparatus, including an instrument having an optical fiber for delivering UV light, an optical viewing fiber and an irregular surface located on the exterior surface at the distal end of the instrument to provide tactile feedback. The instrument preferably additionally comprises an irrigation channel, a suction channel, and abrasives on the distal end of the device. Other aspects of the invention include inventive dental procedures, facilitated by the apparatus, including the cleaning of teeth, periodontic and endodontic procedures, and bleaching discolored teeth.

4 Claims, 5 Drawing Sheets

U.S. PATENT DOCUMENTS

| | | |
|---|---|---|
| 5,240,415 | 8/1993 | Haynie . |
| 5,242,387 | 9/1993 | Loughlin . |
| 5,242,437 | 9/1993 | Everett et al. . |
| 5,267,856 | 12/1993 | Wolbarsht et al. . |
| 5,267,996 | 12/1993 | Fletcher . |
| 5,267,997 | 12/1993 | Farin et al. . |
| 5,281,141 | 1/1994 | Kowalyk . |
| 5,290,274 | 3/1994 | Levy et al. . |
| 5,290,279 | 3/1994 | Bonati et al. . |
| 5,295,832 | 3/1994 | Evans . |
| 5,298,026 | 3/1994 | Chang . |
| 5,300,066 | 4/1994 | Manoukian et al. . |
| 5,300,067 | 4/1994 | Nakajima et al. . |
| 5,300,069 | 4/1994 | Hunsberger et al. . |
| 5,312,399 | 5/1994 | Hakky et al. . |
| 5,324,200 | 6/1994 | Vassiliadis et al. ............ 433/224 |
| 5,328,365 | 7/1994 | Jacoby ............ 433/29 |
| 5,382,163 | 1/1995 | Putnam . |

DENTAL INSTRUMENT AND METHOD OF BLEACHING TEETH USING A LASER

FIELD OF THE INVENTION

This invention relates to dental instruments and is particularly directed to a multi-purpose dental instrument for use in removing intrinsic stains from teeth.

BACKGROUND OF THE INVENTION

The removal of intrinsic stains in the teeth has been found to be very difficult. In an attempt to whiten the stained tooth, the surface of the affected tooth has been painted with oxidizing agents and exposed to special heat or light. Various chemicals applied to the surface of the affected tooth have been tried, for example hydrogen peroxide mixed with other agents such as boric acid, without general success. In addition, the bleaching process itself has been found to be relatively painful.

Some of the difficulties in this process are inherent in all currently available dental techniques. For example, due to the limited range of the hinging of the jaw bone, the dentist must generally rely on tactile, rather than visual, feedback. Likewise, it is extremely difficult to maintain a relatively bacterial free environment due to the bacterial rich flora of the mouth. Finally, most patients have been conditioned to associate the noise of a drill or vibration with pain and, therefore, may react accordingly, even when the process is not painful.

Thus, there is needed an improved dental instrument which facilitates various dental procedures, including the bleaching of teeth, which overcomes the drawbacks of the prior art.

SUMMARY OF THE INVENTION

The present invention is directed to a dental apparatus, and various dental processes facilitated by use of the inventive instrument. In particular, an important aspect of the invention is an improved method of bleaching teeth.

One aspect of the invention is a dental apparatus, including a laser, an instrument connected to the laser comprising a body having a distal end, an optic light delivery fiber and an optic viewing fiber within the body, and an irregular surface at the distal end of the body to provide tactile feedback to the user. The optic delivery fiber is arranged to conduct laser radiation through the instrument to the operative site and the optic viewing fiber is arranged to transmit reflected light from the operative site through the instrument and onto a photodetector. The diameter of the body of the instrument is preferably from about 0.2 to about 10 mm. Desirably, the irregular surface at the distal end of the body comprises one of an abrasive or a rasp, and is made of stainless steel or nickel-titanium.

The instrument facilitates the diagnosis of dental problems by providing the user with both visual and tactile feedback. Additionally, the abrasive or rasp at the distal end of the instrument allows the instrument to be used to remove unwanted material, such as decayed tooth or plaque. Advantageously, the laser source connected to the instrument provides a beam sufficient to cut tissue, so that the laser can also be used as a cutting tool as well as a source of light. Desirably, the laser emits UV light of a wavelength which has a bacteriocidal effect.

The optic delivery fiber of the dental instrument is preferably connected at its proximal end to an Excimer laser. The Excimer laser delivers ultraviolet light in the range of 380–100 nm, and is preferably selected from the group consisting of a Xenon-Fluorine Excimer laser, an Argon-Chlorine Excimer laser, a Xenon-Chlorine Excimer laser, a Krypton-Iodine Excimer laser, and an Argon-Fluorine Excimer laser. Furthermore, although the optic delivery fiber can be comprised of a substance selected from the group consisting of quartz, glass, plastic, and fused silica, it is desirably comprised of quartz which provides excellent transmission of UV light.

The optical viewing fiber preferably reflects light onto a photodetector to facilitate viewing. The photodetector can be a dentist's eye or a charge coupled device.

Preferably, the irrigation channel conducts fluid through the body of the dental instrument from the proximal end to the distal end. The irrigation channel is in fluid communication with a source of fluid external to the proximal end of the body. In addition, the suction channel conducts liquids and solids through the body from the distal end to the proximal end, and is in fluid communication with a source of negative pressure external to the proximal end of the body.

In accordance with another aspect of the present invention, there is provided a method of performing periodontic dental procedures using a dental instrument comprising a fiber optic delivery channel, a fiber optic viewing channel, an irrigation channel, a suction channel and an abrasive surface. The method involves inserting the dental instrument into a patient's mouth, visualizing a portion of a patient's mouth by causing ultraviolet light to be transmitted through the fiber optic delivery channel and into the patient's mouth where it is reflected into the fiber optic viewing channel and transmitted onto a photodetector, identifying a work area within the patient's mouth having carious tissue therein, removing the carious tissue by transmitting laser light through the fiber optic delivery channel to ablate the carious tissue, irrigating the work area by delivering liquid to the work area through the irrigation channel, and suctioning away liquid through the suction channel.

In accordance with still another aspect of the present invention, there is provided a method of bleaching a tooth using a dental instrument comprising a fiber optic delivery channel, a fiber optic viewing channel, and an irrigation channel. The method comprises inserting the dental instrument into a patient's mouth, visualizing a portion of a patient's mouth containing a darkened stained tooth by causing light to be transmitted through the fiber optic delivery channel and into the patient's mouth where it is reflected into the fiber optic viewing channel and onto a photodetector, forming a hole in the stained tooth using laser light transmitted through the fiber optic delivery channel, thereby providing access to pulp inside the stained tooth, delivering a bleaching solution through the irrigating channel and through the hole into the pulp, and photolyzing the bleaching solution by delivering laser light through said fiber optic delivery channel, and into the pulp.

Preferably, the method further comprises hollowing out the stained tooth using laser light delivered through the fiber optic delivery channel to vaporize dentin and pulp within the stained tooth prior to delivering the beaching solution. The hole formed in the tooth is preferably filled and sealed following the photolyzing step.

In accordance with yet another aspect of the present invention, there is provided a dental instrument for bleaching teeth, comprising a tubular body having a distal end and a proximal end, a fiber optic delivery channel extending through said body from the distal to the proximal end for conducting laser radiation through the instrument, and a fluid delivery channel extending through the body from the distal end to the proximal end for delivering fluid through the instrument.

In accordance with still another aspect of the present invention, there is provided a method of bleaching a tooth using a dental instrument comprising a fiber optic delivery channel in communication with an Excimer laser and a fluid delivery channel. The method comprises forming a hole in the tooth to provide access to a pulp chamber within the tooth, positioning the dental instrument inside the hole, delivering a bleaching solution through the fluid delivery channel and into the pulp chamber, and delivering ultraviolet light produced by the Excimer laser through the fiber optic delivery channel and into the pulp chamber to photolyze the bleaching solution.

DETAILED DESCRIPTION OF THE PREFERRED EMBODIMENTS

Figure 1:
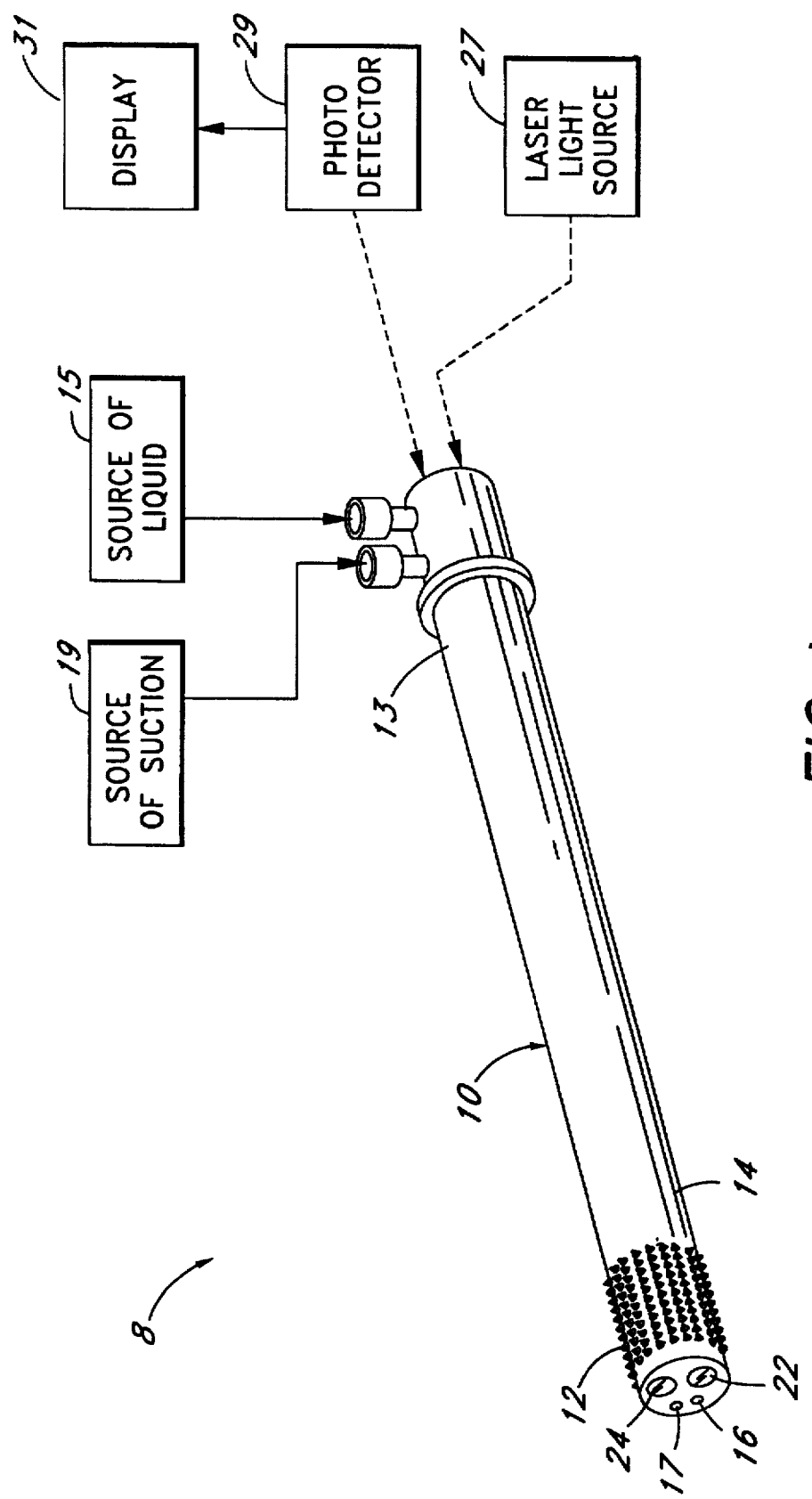
FIG. 1 is a perspective view of a preferred embodiment of the apparatus of the present invention.
Figure 2:
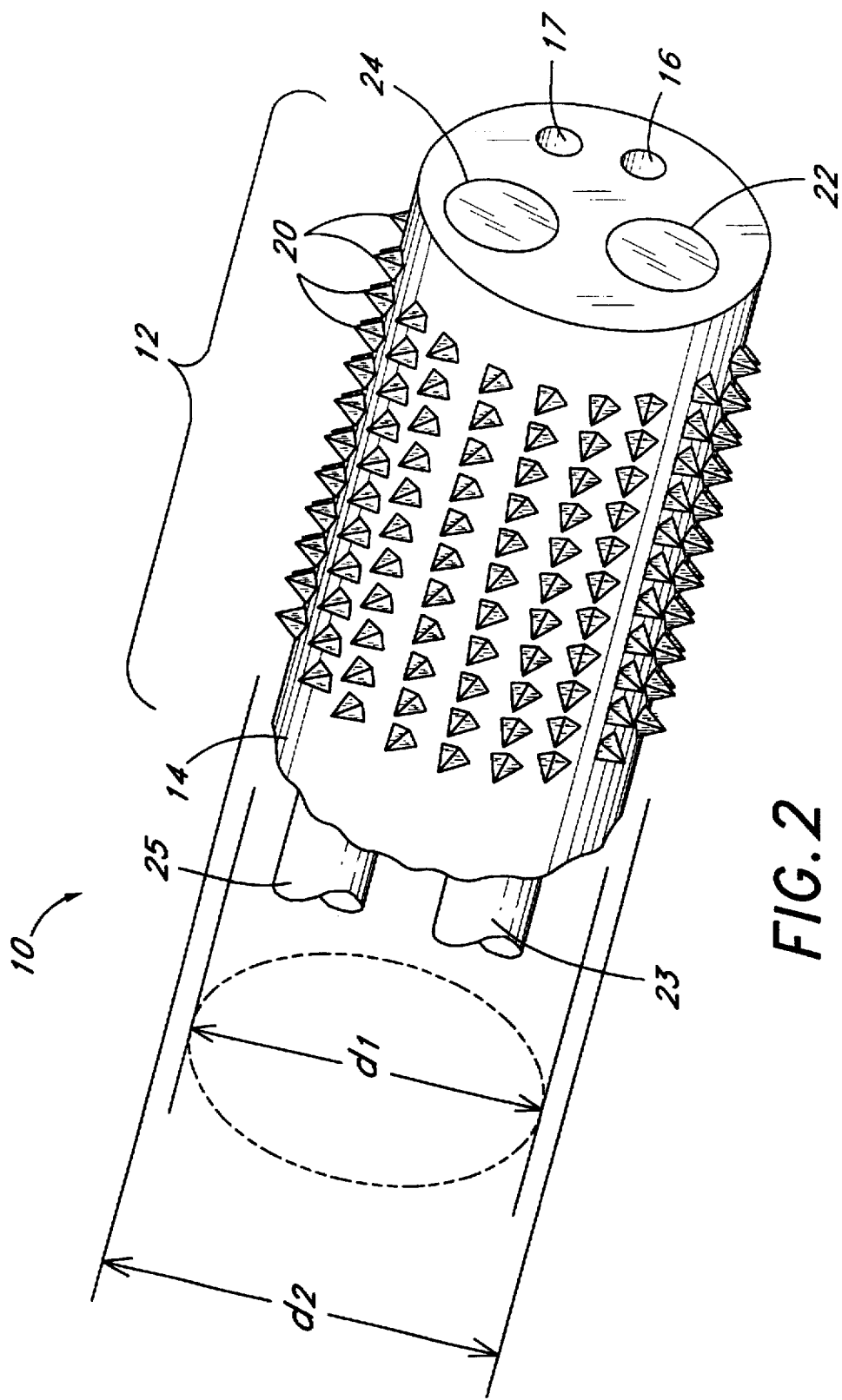
FIG. 2 is an enlarged perspective view of the distal end of the dental instrument of the apparatus of FIG. 1.

Referring FIGS. 1–2, there is shown a dental apparatus 8 of the present invention, including a dental instrument 10, particularly adapted to perform the bleaching method of the present invention. As discussed below, the dental instrument is connected to a number of support devices, which facilitate the operation of the instrument 10.

The housing or body 14 of the dental instrument 10 is a rigid tube or endoscope defining an external diameter $d_1$ defining a smooth outer surface. The external diameter $d_1$ is preferably from about 0.2 mm to about 10.0 mm. The instrument 10 has a tip or distal end 12, which is the operative end of the instrument (i.e., the end used to diagnose or perform dental procedures on the patient), and a proximal end 13, which is opposite the distal end and typically remains outside the mouth of the patient during operation.

Desirably, the tip 12 is provided with a cylindrical external rasp 20, or external abrasives for rasping teeth and bone. Preferably, the external diameter $d_1$ of the rasp 20, which is identified as $d_2$ in FIG. 2, is from approximately 0.1 mm to about 1.0 mm larger than the external diameter of body of the endoscope and the rasp 20 is made from stainless steel or nickel-titanium. However, other sizes and comparable materials may also be used.

An important aspect of the present invention is use by the instrument 10 of a fiber optic system to visually represent the operative dental site. As shown in FIG. 2, the fiber optic system comprises an internal fiber optic delivery channel 22 and an internal fiber optic viewing channel 24 defined by the endoscope, as well as a first optic light delivering fiber 23 and a second optic viewing fiber 25. Desirably, the fibers are made from quartz, due to the nature of light desirably transmitted thereby. The endoscope essentially sheathes the fibers, thereby acting as a cladding for the fibers to protect against surface contaminant scattering.

Preferably, the endoscope also defines an irrigation channel 16 and a suction channel 17. The purpose and significance of these channels will be described below.

The fiber optic light delivering fiber 23 is desirably connected to a source of radiant power, such as a laser light source 27. In particular, an important aspect of the present invention is the use of a source of UV light and, in particular, an Excimer laser as the source of radiant power. Specifically, the Excimer laser is a pulsed gas laser that delivers high peak powers in the ultraviolet spectral region. Specifically, the Excimer laser delivers ultraviolet light in the range of 380–100 nanometers. Examples of such types of Excimer lasers include a Xenon-Fluorine (XeF) Excimer laser (with a wavelength of 351 nm), an Argon-Chlorine (ArCl) Excimer laser (with a wavelength of 175 nm), and a Xenon-Chlorine (XeCl) Excimer laser (with a wavelength of 308 nm). However, Excimer lasers such as Krypton-Iodine (KrI) and Argon-Fluorine (ArF), having wavelengths of 185 nm and 193 nm, respectively, may also be used. The power emitted by the Excimer laser enables it to cut soft tissue and ablate calcium almost totally devoid of any thermal effect. Thus, the Excimer laser can substitute for a dental drill, thereby eliminating the pain and vibration normally associated with dental procedures.

In addition to its tissue cutting and ablating capabilities, the dental instrument 10 can also be used to achieve a bacteriocidal effect. Due to the particular wavelengths of UV light emitted by an Excimer laser, in particular between 303 nm and 351 nm, the Excimer laser provides an efficient and thorough means by which decayed teeth and the surrounding areas may be sterilized. Although Argon ion, Carbon Dioxide and Neodymium-YAG (yttrium aluminum garnet) lasers have shown limited success in the area of sterilization, Excimer lasers have been found to be more effective in controlling micro-organisms due to the sterilization effects of UV radiation. Thus, the dental instrument 10 of the present invention has the capability of inducing a relatively sterile field in the area in which the dental procedure is to be performed. Accordingly, the risk of complications from infection commonly associated with use of conventional dental equipment is reduced.

The benefits associated with the maintenance of a relatively bacterial free preparation of the mouth prior to the restoration of cavities or endodontic work are numerous. For example, it is estimated that as many as twenty percent of all root canals are complicated by infection. The problem of infection following a root canal procedure requires the urgent, painful and costly reopening of the gum and bone overlying the affected root or the turning of a flap. By providing a relatively bacterial free environment, it is anticipated that the rate of infection from dental procedures can be substantially reduced, thereby reducing pain associated with the procedures and reducing costs.

When exposed to light, the tissue of the patient's mouth will both absorb and reflect the light. The fraction of the light that is absorbed by the tissues is converted into heat. The heat can be used to create a hole in the tissues or for therapeutic purposes. The remainder of the light is reflected and scattered by the tissues. Light scattering and reflection is based upon light wavelength. The light is reflected (usually at a different wavelength) into the fiber optic viewing fiber 24 and onto a photodetector 29.

The photodetector can comprise a dentist's eye, but preferably comprises a charge coupled device used in a TV camera for magnifying and recording the areas being viewed. Enhanced surface imaging can be accomplished via a computer data acquisition system, as is well known to those of ordinary skill in the art. The visual image can then be projected on a display for viewing by the dentist. For example, the device can be configured as a tandem scanning microscope for real-time direct viewing, or as a confocal scanning microscope for low-level fluorescence work.

The irrigation channel 16 is housed within the dental instrument 10 to aid the dentist throughout the dental procedure. During certain procedures, such as periodontic cleaning, it becomes necessary for the dentist or technician to irrigate the area undergoing treatment so as to clear away debris. Thus, the irrigation channel 16, which is attached to a source of liquid 15, allows the dentist to irrigate the treatment area with liquid when necessary.

An additional function of the irrigation channel 16 is to cool the fiber optic channel 22 housed within the dental instrument 10. Due to the light intensity and amount of energy transmitted through the fiber optic delivering channel 22, a significant amount of heat is generated. Thus, the fiber 22 and/or its surrounding area should preferably be cooled in order to prevent the fiber 22 from being damaged by the heat. For the dental instrument 10 of the present invention, the irrigation channel 16 is positioned along the axial length of the dental instrument 10 and adjacent to the fiber optic channel 22. Cool liquid, delivered through the irrigation channel 16, absorbs the heat emitted along the length of the fiber optic channel 22.

The irrigation channel 16 can also be used to cool the tissues being irradiated by the laser light. Delivery of a cooling fluid to the tissue lessens the heat generated by the laser radiation and helps reduce the damage caused to surrounding tissues.

Thus, the irrigation channel 16 serves to substantially cool the fiber optic channel 22 of the dental instrument 10, and the tissues being irradiated by the laser light, and also provides a source of liquid used to irrigate the patient's mouth to remove debris.

The suction channel 17 of the dental instrument 10 is desirably connected to a source of suction 19, such as a pump or other source of negative pressure. Certain dental procedures, such as plaque removal procedures and extractions, require that waste such as plaque, blood and excess saliva be removed from the patient's mouth. Thus, the suction channel 17 allows the dentist to remove the waste, thereby clearing the theater in which the dental instrument 10 is being used.

As discussed above, some dental procedures require that the area being worked on be irrigated by liquid delivered from some form of an irrigation means. In order to prevent the liquid from obstructing the area being worked on by the dentist and the excess liquid uncontrollably draining from the patient's mouth, a separate suction device is typically employed by the dentist. However, this typically requires that the dentist periodically interrupt his or her work to adjust the location of the suction device in the patient's mouth. By incorporating the suction means into a dental instrument, as with the dental instrument 10 of the present invention, the excess liquid and waste is removed without interrupting the dental procedure. Thus, the disclosed embodiment provides an efficient and convenient means whereby waste and excess liquid is removed from a dental patient's mouth.

The combination of the suction 17 and irrigation 16 channels, and the abrasives 20 conveniently located on the distal end of the dental instrument 10, provide the dentist with a multipurpose tool.

Operation

Figure 3:
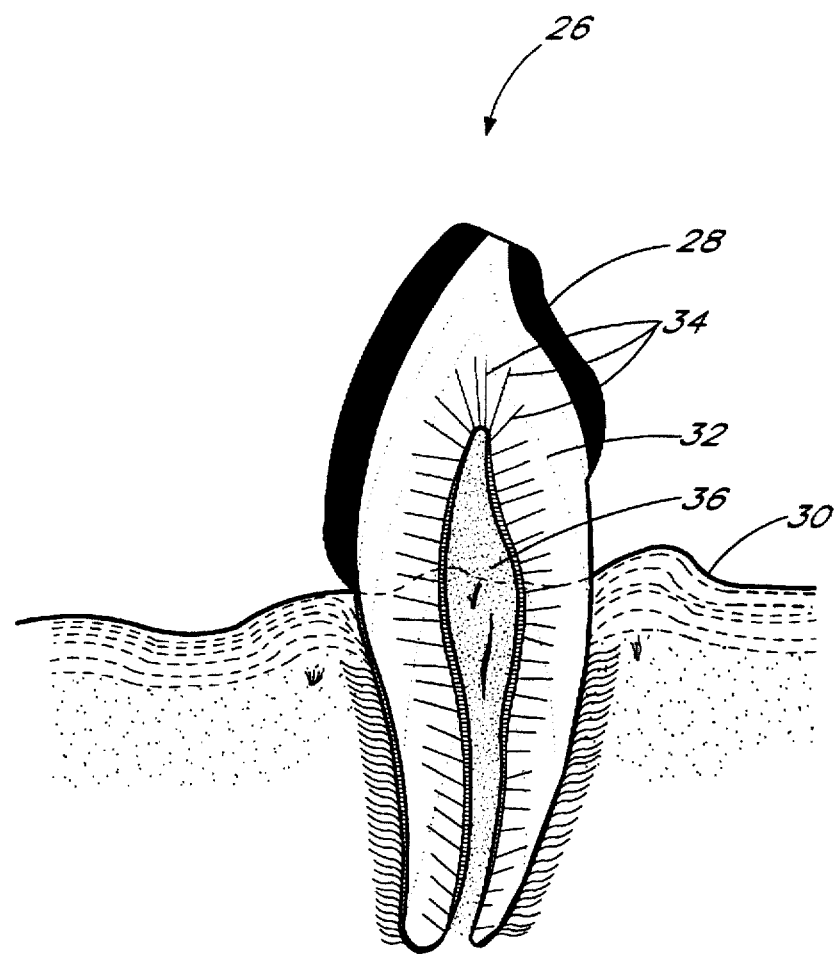
FIG. 3 is a cross-sectional side view of a normal tooth.

The dental instrument 10 of the present invention is particularly advantageous for use in the bleaching of discolored teeth. Both the surface of the teeth and their internal structures are subject to the possibility of staining. FIG. 3 shows a cross-sectional side view of a normal tooth 26. The outer surface of the tooth 26 is covered with enamel 28, a hard, protective coating. Enamel 28 is the hardest tissue in the body, due to the high concentration of mineral salts, and it contains no nerve supply. The enamel 28 covers the exposed surface of the tooth 26 and does not continue beneath a gumline 30. The enamel 28 is nourished, to a slight degree, from the underlying bone-like tissue, dentin 32. Dentin 32, which is comprised of small channels called dentinal tubules 34 which are 2–3 microns in length, makes up the bulk of the tooth 26 and is highly sensitive due to its rich nerve supply. Pulp 36, located in the center of the tooth 26 and surrounded by the dentin 32, is comprised of nerves, fibrous tissue, lymph and blood vessels.

Extrinsic and intrinsic stains occur as a result of the variety of substances brought into contact with the teeth through the mouth or carried by the blood supply. Extrinsic stains, found on the surface of the teeth, are easily removed by polishing and may be prevented by regular brushing and good dental hygiene. Intrinsic stains, however, are found in the inside areas of the teeth, and are more difficult to remove. Intrinsic staining or darkening of the teeth is a common occurrence and may result from the death of the pulp 36 or the removal of the pulp 36 during root canal treatment. Various necrotic substances defuse from the pulp chamber, penetrating the dentin 32 and staining the tooth 26. These products enter into the dentinal tubules 34 and impart a total darkening into the crown or tooth 26 from enamel 28 reflection. Prior techniques for removing intrinsic stains have been difficult, and largely unsuccessful. However, by utilizing the specific features and capabilities of the instrument 10 of the present invention together with a chemical solution, intrinsic stains can be successfully removed.

Figure 4:
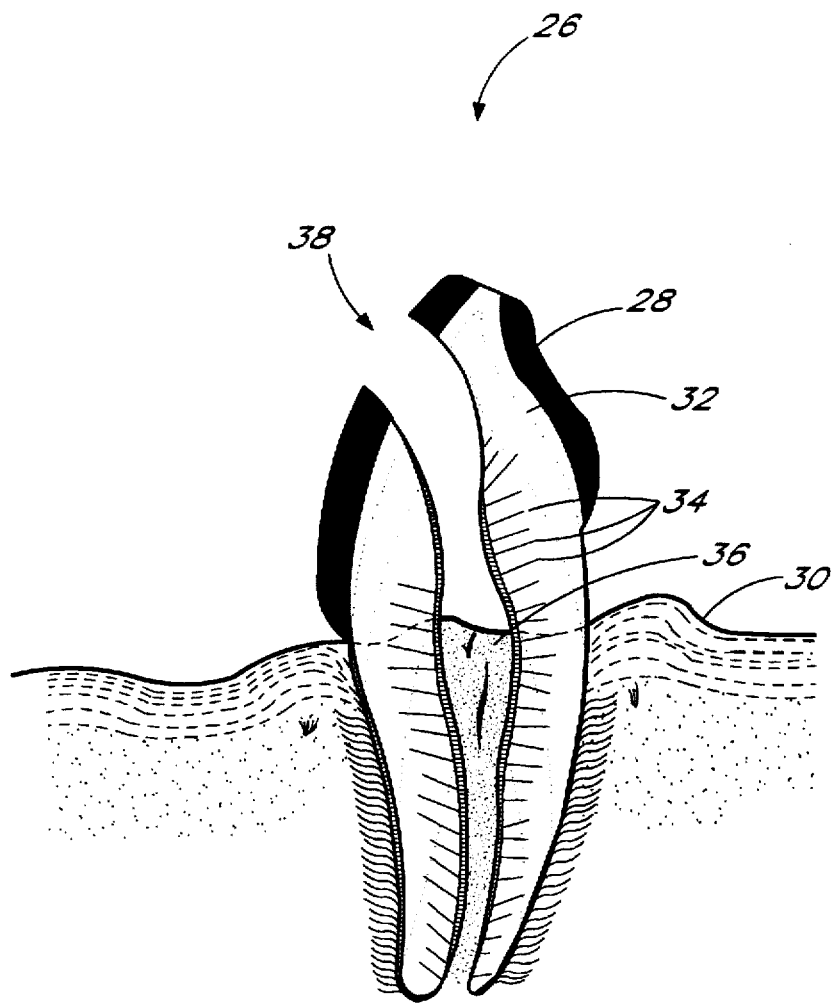
FIG. 4 is a cross-sectional side view of a tooth having a hole through its surface and the pulp removed in accordance with the dental procedure of the present invention.
Figure 5:
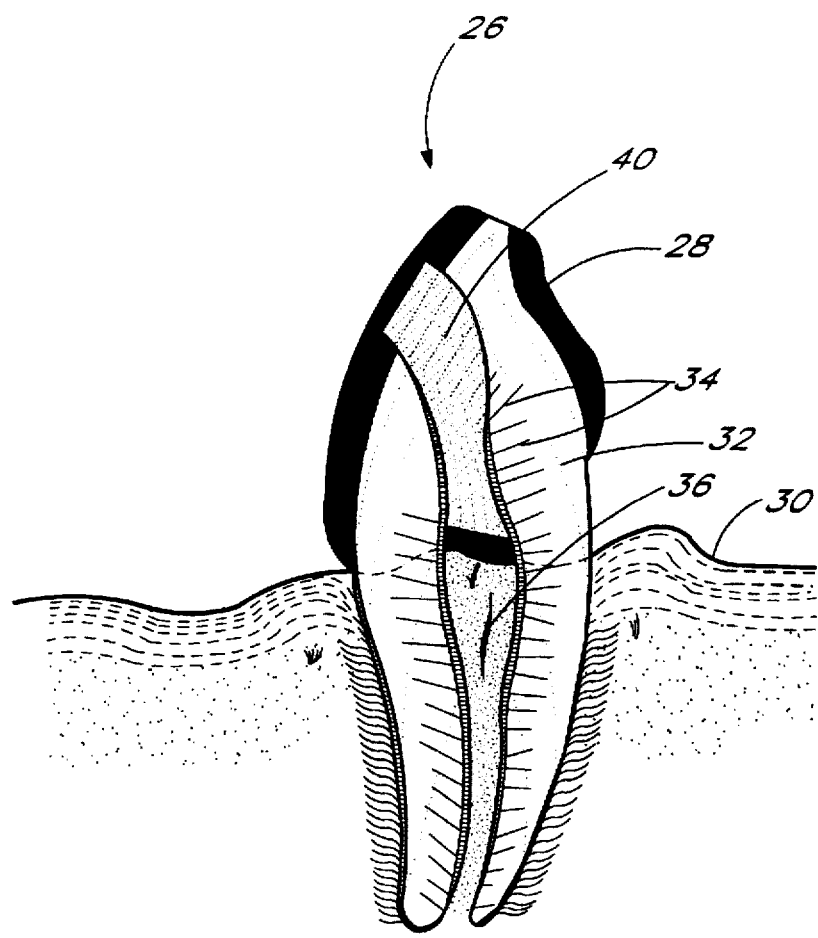
FIG. 5 is a cross-sectional side view of the tooth of FIG. 4 after completion of the dental procedure of the present invention.

As illustrated in FIGS. 4 and 5, the dental instrument 10 of the present invention is first used to cut a canal or hole 38 in the tooth 26. This is accomplished by utilizing the abrasives 20 located on the distal portion of the dental instrument 10. By rotating the dental instrument 10 about its longitudinal axis or by moving the dental instrument 10 along its longitudinal axis, the abrasives 20 scrape and wear away a portion of the enamel 28 from the tooth 26. Alternatively, laser light can be delivered via the fiber optic UV channel 22 and can be used to provide access to the pulp chamber 36.

Next, the Excimer laser is used to deliver radiation which ablates or vaporizes a portion of the dentin 32 and all of the pulp 36 up to the gumline 30, as shown in FIG. 4. This is accomplished by utilizing both the optical delivery fiber 23 and the optical viewing fiber 25. A predetermined wavelength of light is emitted from the delivery fiber 23 at the tip 12 of the dental instrument 10 and impinges onto the target area. Subsequently, some of the light is absorbed by the tissues and the remainder of the light is reflected or scattered by the tissues. The reflected light, however, is of a different wavelength from the emitted light. In addition, the wavelength of reflected light varies according to the tissue type. Thus, the wavelength of light reflected by the dentin 32 is different from the wavelength of light reflected by the pulp 36. The reflected light is transmitted through the optical viewing fiber 25 and onto a photodetector 29, or photodetector 29 and display 31 where it is analyzed. Thus, the dentist or technician is able to determine when all of the dentin 32 and pulp 36 have been removed, based upon the wavelength of reflected light.

Alternatively, the abrasives 20 located on the exterior surface of the tip 12 of the dental instrument 10 can also be used to file or remove the pulp 36 within the tooth 26.

After the hole 38 has been made in the tooth 26, the hole 38 is filled with a chemical bleaching solution, preferably comprising hydrogen peroxide and ethanol. The bleaching solution may be delivered into the hole 38 in the tooth 26 via the irrigation channel 16 located within the dental instrument 10 of the present invention. The irrigation channel 16, which conducts fluid through the body 14 of the dental instrument 10 from its proximal end to its distal end, is attached at its proximal end to an external source containing the chemical bleaching solution. A button, switch or foot pedal is depressed thereby causing the solution to be dispensed from the dental instrument 10 into the hole 38 in the tooth 26.

The Excimer laser 27 is then used to deliver ultraviolet light to the chemical solution within the tooth 26. By utilizing the viewing channel 24, the dentist or technician is able to accurately position the dental instrument 10 so that the beam of laser light is focused into the solution in the hole 38 in the patient's tooth 26.

The use of light or other radiant energy to induce chemical decomposition is known as photolysis. For the present invention, UV laser light is used to photolyze the hydrogen peroxide while the hydrogen peroxide is in the hole 38 in the patient's tooth 26. The UV photolysis of the hydrogen peroxide generates perhydroxyl ($HO_2$) and superoxide ($O_2^-$) radicals, which are very effective bacteriocidal, as well as bleaching, agents. In order to increase the quantum yield of free radical formation and, thereby, promote a more complete and efficient bleaching and bacteriocidal effect, a free radical scavenger is preferably added to the hydrogen peroxide solution. Scavengers such as formate and ethanol may be used, however for the preferred embodiment of the present invention, ethanol is combined with the hydrogen peroxide. In the presence of oxygen and scavengers such as formate or ethanol, the primary radicals are converted to superoxide radicals, resulting in an increase in the yield of free radical formation. In accordance with the present invention, the laser light photoactivates the hydrogen peroxide and ethanol solution, thereby generating perhydroxyl and superoxide radicals. The generation of free radicals promotes "bleaching" of the dentinal tubules 34, thereby resulting in a white tooth 26 which is relatively free from intrinsic stains. The reaction mechanism and experimental conditions under which these reactions occur have been extensively studied and are well known to those of skill in the art.

After the tooth 26 has been bleached, the hole 38 in the tooth 26 should be filled and sealed to prevent contamination and subsequent darkening of the tooth 26. Initially, the hole 38 is filled with cavite, a material used as a temporary filling. Amalgam, a metallic compound usually used to fill molars, or, alternatively, a white plastic or composite material, is later used for a permanent filling 40, as shown in FIG. 5. Thus, the dental instrument 10 of the present invention together with a bleaching solution, such as hydrogen peroxide and ethanol, provides a very potent and improved system for the bleaching of teeth.

Another aspect of the invention is a method of plaque removal. Conventional plaque removal requires that the dentist or dental technician's work be interrupted periodically so that the patient can rinse his or her mouth to clear away debris. In addition, various suction and irrigation tools are also commonly used by dentists or technicians to aid in cleaning and the removal of debris. Once this is accomplished, the area being worked on within the patient's mouth is clean, and the dentist or technician can continue removing the remaining plaque.

With the present invention, however, the dentist or technician's work does not need to be interrupted. The debris generated from the cleaning procedure can be removed while the dentist or technician continues with the procedure. As the abrasives 20 located on the distal end of the dental instrument 10 rasp the surface of the patient's teeth, the irrigation channel 16 can irrigate the area being worked on so as to clean and, concurrently, cool the area undergoing treatment. Subsequently, the suction channel 17 can clear away the debris obscuring the operative field. Thus, this entire function can be performed conveniently and efficiently without interrupting the dentist's or technician's work.

The benefits of the present invention are numerous. By simultaneously rasping the teeth, irrigating the work area and suctioning away the debris, the entire dental procedure can be performed in less time than that required for conventional dental procedures. This, in turn, provides a cost savings to the patient. In addition, since the area being worked on is more frequently cleaned due to the ability of the dental instrument 10 to simultaneously irrigate and suction the area when using the dental instrument 10, there is less likelihood of infection or adverse reactions occurring. Finally, the patient is no longer subjected to the unpleasant feeling of a gritty solution of abrasives, plaque and water normally encountered during the rinsing of his or her mouth.

Other dental procedures, such as cavity restoration and root canals, may also be performed using the dental instrument 10 of the present invention. Dental caries or tooth decay result from the gradual erosion of enamel 28 and dentin 32 caused by plaque. Treatment of dental caries requires the removal of the decayed area of the tooth 26 and the repair of the resultant hole or cavity with a dental restoration compound, such as amalgam or cement. The abrasives 20 located at the distal end of the dental instrument 10 may be used to rasp and, subsequently, remove the decayed portion of the enamel 28 and/or dentin 32 of the tooth 26. Alternatively, or in combination with the abrasives 20, the UV laser light emitted by the fiber optic delivery channel 22 may be focused onto the decayed area to ablate the dental caries.

Advanced tooth decay, resulting in the death of the pulp 36, may require the complete removal of the pulp 36. Conventional root canal procedures involve drilling a hole 38 in the tooth 26 to remove the infected material from the pulp chamber 36, filling the hole 38 with paste and cement and fitting a crown over the hole 38. By using the dental instrument 10 of the present invention, the patient is no longer subjected to the pain and discomfort associated with conventional root canal drilling procedures. The dentist or technician uses the abrasives 20 and/or laser light delivered by the fiber optic delivery channel 22 to remove the infected pulp 36. After the infected material has been removed, the resultant hole 38 is filled with paste and cement and fitted with a crown, or otherwise sealed.

Additionally, throughout the cavity restoration and root canal procedures, the target area may be irrigated by a liquid delivered by the irrigation channel 16 and waste removed utilizing the suction channel 17 of the dental instrument 10 of the present invention.

Obviously, numerous variations can be made without departing from the spirit of the present invention. Therefore, it should be clearly understood that the forms of the present invention described above are illustrative only and not limiting.

What is claimed is:

1. A method of bleaching a tooth using a dental instrument comprising a fiber optic delivery channel, a fiber optic viewing channel, and an irrigation channel, said method comprising the steps of:

inserting the dental instrument into a patient's mouth;

visualizing a portion of a patient's mouth containing a darkened or stained tooth by causing light to be transmitted through a fiber optic delivery channel in said dental instrument and into the patient's mouth where it is reflected into a fiber optic viewing channel in said dental instrument and onto a photodetector;

forming a hole in a stained tooth using laser light transmitted through said fiber optic delivery channel, thereby providing access to pulp inside a stained tooth;

delivering a bleaching solution through an irrigating channel in said dental instrument and through said hole; and photolyzing said bleaching solution by delivering laser light into said solution through said fiber optic delivery channel, through said hole.

2. The method of claim 1, further comprising hollowing out a stained tooth using laser light delivered through said fiber optic delivery channel to vaporize dentin and pulp within a stained tooth prior to delivering said bleaching solution.

3. The method of claim 1, further comprising filling and sealing said hole following said photolyzing step.

4. A method of bleaching a tooth using a dental instrument comprising a fiber optic delivery channel in communication with an excimer laser and a fluid delivery channel, comprising the steps of:

forming a hole in a tooth to provide access to a pulp chamber within;

positioning said dental instrument inside said hole;

delivering a bleaching solution through said fluid delivery channel and into a pulp chamber; and delivering ultraviolet light produced by an excimer laser through a fiber optic delivery channel in said dental instrument to photolyze said bleaching solution.

* * * * *